United States Patent [19]

Sakuta

[11] Patent Number: 5,236,986
[45] Date of Patent: Aug. 17, 1993

[54] SILICONE POLYMERS AND WATER-DISPERSABLE, PASTY SILICONE OIL COMPOSITIONS COMPRISING THE SAME

[75] Inventor: Koji Sakuta, Annaka, Japan

[73] Assignee: Shin-Etsu Chemical Co., Ltd., Tokyo, Japan

[21] Appl. No.: 842,689

[22] Filed: Feb. 27, 1992

[30] Foreign Application Priority Data

Feb. 27, 1991 [JP] Japan .................................. 3-56033

[51] Int. Cl.$^5$ .............................................. C08K 5/54
[52] U.S. Cl. .................................. 524/267; 525/478; 556/479; 528/15; 528/25
[58] Field of Search .................... 528/15, 25; 556/479; 525/478; 524/267

[56] References Cited

U.S. PATENT DOCUMENTS

| | | | |
|---|---|---|---|
| 4,877,854 | 10/1989 | Hatori et al. ........................... | 528/15 |
| 4,987,169 | 1/1991 | Kuwata . | |
| 5,036,123 | 7/1991 | Ozaki et al. .......................... | 524/265 |
| 5,138,009 | 8/1992 | Ioue ..................................... | 528/15 |

FOREIGN PATENT DOCUMENTS

| | | |
|---|---|---|
| 0298402 | 1/1989 | European Pat. Off. . |
| 0420253A2 | 4/1991 | European Pat. Off. . |
| 4010281A1 | 10/1990 | Fed. Rep. of Germany . |
| 62-45656 | 2/1987 | Japan . |
| 62-54759 | 3/1987 | Japan . |
| 62-121764 | 6/1987 | Japan . |
| 62-143971 | 6/1987 | Japan . |
| 62-240335 | 10/1987 | Japan . |
| 63-727779 | 4/1988 | Japan . |
| 63-152308 | 6/1988 | Japan . |
| 63-159489 | 7/1988 | Japan . |
| 63-260955 | 10/1988 | Japan . |
| 62143970 | 6/1989 | Japan . |
| 1-207354 | 8/1989 | Japan . |
| 2-43263 | 2/1990 | Japan . |

*Primary Examiner*—Melvyn I. Marquis
*Attorney, Agent, or Firm*—Lowe, Price, LeBlanc & Becker

[57] ABSTRACT

A novel silicone polymer which is obtained by addition polymerization of at least one organohydrogenpolysiloxane of the type shown below $$R^1_a R^2_b H_c SiO_{(4-a-b-c)/2} \quad (1)$$

$$R^1_j H_k SiO_{(4-j-k)/2} \quad (2)$$

and a specific type of polyoxyalkylene and/or organopolysiloxane provided that at least one selected from the organohydrogenpolysiloxane of the general formula (1) and the polyoxyalkylene is present for the addition polymerization. The silicone polymer is capable of being swollen with silicone oils to give a uniform, pasty composition without use of any surface active agent. This composition is able to stably, uniformly disperse water therein. Thus, the silicone polymer has wide utility in the fields of cosmetics and medicines.

26 Claims, No Drawings

SILICONE POLYMERS AND WATER-DISPERSABLE, PASTY SILICONE OIL COMPOSITIONS COMPRISING THE SAME

BACKGROUND OF THE INVENTION

1. Field Of The Invention

This invention relates to novel silicone polymers which are swollen with silicone oils and also to pasty silicone oil compositions which comprise the silicone polymers and silicone oils and are capable of stably and uniformly dispersing water therein.

2. Description of The Prior Art

Silicone oils are non-toxic and have thus wide utility in various fields including medicines and cosmetics, as base oils for a variety of compositions. In general, silicone oils have a relatively high viscosity of not lower than 100 centistokes at 25° C. Especially, in the fields of medicines and cosmetics, attention has been recently drawn to silicone oils which have a low viscosity of not higher than 100 centistokes because of their good extensibility, cool or refreshing touch and high safety. Hence, extensive studies have been made on the applications of such silicone oils.

However, when low viscosity silicone oils are used as a base oil to prepare, for example, pasty or greasy compositions, it is necessary to add thickening agents in amounts larger than in the case using ordinary silicone oils. This makes it difficult to obtain a homogeneous, uniform composition, with the attendant problem that the low viscosity silicone oil is liable to separate from the composition with low stability of the composition.

In order to solve these problems, attempts have been heretofore made wherein various types of thickening agents for the low viscosity silicone oils are proposed including organic materials such as fatty acid esters of dextrin (Japanese Laid-open Application Nos. 62-121764, 62-143971, 62-143970 and 63-159489), fatty acid esters of sucrose (Japanese Laid-open Patent Application No. 63-235366), trimethylsilylated polyvinyl alcohol or trimethylsilylated polysaccharides (Japanese Laid-open Patent Application No. 62-240335), fatty acid ester group-containing cellulose ethers (Japanese Laid-open Patent Application No. 63-260955) and the like, and inorganic materials such as organic modified clay minerals (Japanese Laid-open Patent Application Nos. 62-45656, 62-54759 and 63-72779).

However, the use of these organic or inorganic materials as a thickening agent involves the problem that the inherent characteristics of the silicone oil such as the refreshing or cool touch to the skin and the high extensibility are reduced.

Another approach has been proposed, for example, in Japanese Laid-open Patent Application No. 2-43263, wherein a specific type of silicone polymer is provided as a thickening agent and treated along with low viscosity silicone oils under shearing conditions to obtain a uniform pasty composition.

In the fields of medicines and cosmetic articles, there are often used compositions which are formulated not only with oils, but also with water as essential ingredients. In such a case, it is usual to add surface active agents to the composition. However, a difficulty is still involved in dispersing silicone oils and water uniformly and stably. In addition, most surface active agents are irritative to the skin and their use is not favorable. Although the silicone thickening agent set forth in the Japanese Laid-open Patent Application No. 2-43263 exhibits good thickening properties against silicone oils, water is not uniformly dispersed therein.

SUMMARY OF THE INVENTION

It is accordingly an object of the invention to provide a novel silicone polymer which is able to thicken low viscosity silicone oils thereby making a paste or greasy composition comprising such low viscosity silicone oils.

It is another object of the invention to provide a pasty silicone oil composition wherein water can be uniformly, stably dispersed in the composition without use of any surface active agent.

The above objects can be achieved, according to the invention, by a silicone polymer which is obtained by addition polymerization of (i) at least one organohydrogenpolysiloxane selected from the group consisting of those of the general formulas (1) and (2)

$$R^1_a R^2_b H_c SiO_{(4-a-b-c)/2} \quad (1)$$

$$R^1_j H_k SiO_{(4-j-k)/2} \quad (2)$$

and (ii) at least one member selected from the group consisting of a polyoxyalkylene of the general formula (A)

$$C_m H_{2m-1} O(C_2H_4O)_p (C_3H_6O)_q C_m H_{2m-1} \quad (A)$$

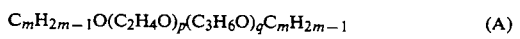

and an organopolysiloxane of the general formula (B)

$$R^1_d R^3_e SiO_{(4-d-e)/2} \quad (B)$$

provided that at least one of the organohydrogenpolysiloxane of the general formula (1) and the polyoxyalkylene of the general formula (A) is present for the addition polymerization, wherein $R^1$'s may be the same or different in the respective formulas and represent an unsubstituted or substituted alkyl group having from 1 to 18 carbon atoms, an aryl group, an aralkyl group or a monovalent halogenated hydrocarbon group, $R^2$ represents an organic group of the general formula, $$C_n H_{2n} O(C_2H_4O)_f (C_3H_6O)_g R^4$$

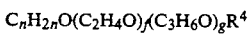

wherein $R^4$ represents a hydrogen atom or a saturated organic group having from 1 to 5 carbon atoms or a group of the formula, $R^5$—(CO)—, in which $R^5$ represents a saturated organic group having from 1 to 5 carbon atoms, each of m and n is an integer of from 2 to 6, f is an integer of from 2 to 200, and g is an integer of from 0 to 200 provided that f+g is in the range of from 3 to 200, $R^3$ represents a monovalent hydrocarbon group having a vinyl end group and having from 2 to 10 carbon atoms, a, b, c, d, e, j and k are, respectively, such that $1.0 \leq a \leq 2.5$, $0.001 \leq b \leq 1$, $0.001 \leq c \leq 1$, $1.0 \leq d \leq 3.0$, $0.001 \leq e \leq 1.5$, $1.0 \leq j \leq 3.0$, and $0.001 \leq k \leq 1.5$, p is an integer of from 2 to 200, and q is an integer of from 0 to 200 provided that p+q is from 3 to 200.

According to another embodiment of the invention, there is also provided a pasty silicone oil composition which comprises a mixture of the silicone polymer defined above and a silicone oil, the mixture being kneaded under shearing conditions sufficient to cause the silicone polymer to be swollen with the silicone oil. The silicone oil should preferably have a viscosity at 25° C. of not higher than 100 centistokes.

EMBODIMENTS AND DETAILED DESCRIPTION OF THE INVENTION

The novel silicone polymer is first described. The silicone polymer is a product obtained by addition polymerization between at least one organohydrogenpolysiloxane selected from those of the general formulas (1) and (2) defined above and at least one of a polyoxyalkylene of the general formula (A) and an organopolysiloxane of the general formula (B) provided that at least one selected from the organohydrogenpolysiloxane of the formula (1) and the polyoxyalkylene of the formula (A) is essentially contained for the addition polymerization.

Examples of the organohydrogenpolysiloxane of the general formula (1) include those organohydrogenpolysiloxanes which have $R^1SiO_{1.5}$ units, $R^1{}_2SiO$ units, $R^1{}_3SiO_{0.5}$ units, $R^2SiO_{1.5}$ units, $R^2R^1SiO$ units, $R^2R^1{}_2SiO_{0.5}$ units, $HSiO_{1.5}$ units, $HR^1SiO$ units and $HR^1{}_2SiO_{0.5}$ units. It is preferred that the organohydrogenpolysiloxane has $R^1{}_2SiO$ units, $R^1{}_3SiO_{0.5}$ units, $R^2R^1SiO$ units, and $HR^1SiO$ units at the same time. The organohydrogenpolysiloxane may be linear, branched or cyclic, of which linear polysiloxanes are preferred in order to cause the addition polymerization to proceed smoothly. This type of organohydrogenpolysiloxane is readily obtained by a procedure as particularly set out in Synthetic Examples 1 appearing hereinafter.

The organohydrogenpolysiloxanes of the general formula (2) are those which have $R^1SiO_{1.5}$ units, $R^1{}_2SiO$ units, $R^1{}_3SiO_{0.5}$ units, $R^1HSiO$ units, $R^1{}_2HSiO_{0.5}$ units, and $HSiO_{1.5}$ units. Preferably, the organohydrogenpolysiloxane of the formula (2) should contain $R^1{}_2SiO$ units, $R^1{}_3SiO_{0.5}$ units, and $R^1HSiO$ units at the same time with or without further mixing with an organohydrogenpolysiloxane composed of $R^1HSi_{0.5}$ units and $S^1{}_2SiO$ units. In this case, the organohydrogenpolysiloxane may be linear, branched or cyclic, of which linear polysiloxanes are preferred in order to cause the addition polymerization to proceed smoothly.

The organopolysiloxanes of the general formula (B) are, for example, those which have $R^1SiO_{1.5}$ units, $R^1{}_2SiO$ units, $R^1{}_3SiO_{1.5}$ units, $R^3{}_2SiO$ units, $R^3SiO_{0.5}$ units, $R^1R^3SiO$ units, $R^1{}_2R^3SiO_{0.5}$ units and $R^1R^3{}_2SiO_{0.5}$ units. The organopolysiloxanes of this form may be linear, branched or cyclic, of which the linear polysiloxane is preferred in order to cause the addition polymerization to proceed smoothly.

In the formulas (1), (2) and (B) and the respective units, each $R^1$ represents an alkyl group having from 1 to 18 carbon atoms, e.g. a methyl group, an ethyl group, a propyl group, a butyl group, a pentyl group, a hexyl group, a heptyl group, an octyl group, a nonyl group, a decyl group or the like, a saturated alicyclic hydrocarbon group having from 5 to 10 carbon atoms, e.g. a cyclopentyl group, a cylohexyl group or the like, an aryl group such as a phenyl group, a tolyl group or the like, an aralkyl group such as a benzyl group, a phenethyl or the like, and a halogenated hydrocarbon group such as a trifluoropropyl group, a heptadecafluorodecyl group, a chloropropyl group, a chlorophenyl group or the like. It is preferred that the methyl group is contained in an amount of not less than 50% of the total of $R^1$'s.

Examples of the aliphatic unsaturated group represented by $R^3$ include a vinyl group, an allyl group and the like, of which the vinyl group is preferred.

Examples of $R^4$ include, aside from a hydrogen atom, saturated aliphatic hydrocarbon groups such as a methyl group, an ethyl group, a propyl group, a butyl group, a pentyl group, a hexyl group, a heptyl group, an octyl group, a nonyl group, a decyl group and the like.

Examples of the group represented by $R^5$ include saturated aliphatic hydrocarbon groups such as a methyl group, an ethyl group, a propyl group, a butyl group, a pentyl group and the like.

In the general formula (1), a is generally in the range of from 1.0 to 2.5, preferably from 1.0 to 2.1 and more preferably from 1.9 to 2.1. If a is smaller than 1, the resultant polymer is not well swollen in the silicone oil. On the contrary, when a is larger than 2.5, a pasty composition which is obtained by kneading or mixing the resulting polymer and a silicone oil under shearing conditions cannot disperse water therein satisfactorily.

The value of b is generally in the range of from 0.001 to 1.0, preferably from 0.005 to 1.0 and more preferably from 0.01 to 0.50. If the value is less than 0.001, the pasty composition of the resulting polymer and a silicone oil cannot satisfactorily disperse water. When the value exceeds 1.0, the resulting polymer is not swollen in silicone oils as desired.

The value of c is generally in the range of from 0.001 to 1.0, preferably from 0.005 to 1.0 and more preferably from 0.01 to 0.10. If the value is smaller than 0.001, it becomes difficult to form a three-dimensional structure in the polymer obtained by the addition polymerization, leading to a poor effect of thickening silicone oils. On the other hand, when the value exceeds 1.0, the crosslinkage density of the three-dimensional structure formed by the addition polymerization becomes too high to stably keep silicone oils.

The value of d is generally in the range of from 1.0 to 3.0, preferably from 1.0 to 2.5 and more preferably from 1.9 to 2.1. If the value is smaller than 1.0, the crosslinkage density of the three-dimensional structure becomes too high with an attendant disadvantage set out above. If the value exceeds 3.0, the three-dimensional structure is not formed in the resultant polymer to a satisfactory extent, so that the silicone oil is not effectively thickened.

The value of e is generally in the range of from 0.001 to 1.5, preferably from 0.005 to 1.0 and more preferably from 0.01 to 0.50. If the value is smaller than 0.001, successful formation of the three-dimensional structure in an intended polymer is not expected, making it difficult to thicken silicone oils as desired. If the value exceeds 1.5, the crosslinkage density of the three-dimensional structure becomes too high to stably keep silicone oils.

The values of p and q in the formula (A) are, respectively, integers in the ranges of from 2 to 200, preferably from 5 to 100 and more preferably from 3 to 20, and from 0 to 200, preferably from 0 to 100 and more preferably from 0 to 20, provided that the value of (p+q) is in the range of from 3 to 200.

The values of f and g in the formula represented by $R^2$ are, respectively, integers in the ranges of from 2 to 200, preferably from 5 to 100 and more preferably from 3 to 20, and from 0 to 200, preferably from 0 to 100 and more preferably from 0 to 20, provided that the value of (f+g) is in the range of from 3 to 200.

In order to permit a pasty composition obtained by kneading the resultant polymer and a silicone oil under shearing conditions to be satisfactorily dispersed, it is preferred that $f/g \geq 1$ and/or $p/q \geq 1$.

The values of j and k in the formula (2) are as follows.

The value of j is generally in the range of from 1.0 to 3.0, preferably from 1.0 to 2.5 and more preferably from 1.9 to 2.1. If the value is smaller than 1.0, the resultant polymer is not swollen in silicone oils satisfactorily. Over 3.0, it becomes difficult to form a three-dimensional structure in the polymer obtained by the addition polymerization. Thus, it will not be expected to thicken silicone oils.

The value of k is generally in the range of from 0.001 to 1.5, preferably from 0.005 to 1.0 and more preferably from 0.01 to 0.10. If the value is smaller than 0.001, satisfactory formation of the three-dimensional structure is not expected with the attendant disadvantage that silicone oils cannot be thickened effectively. When the value exceeds 1.5, the crosslinkage density of the three-dimensional structure formed by the addition reaction becomes too high to stably retain silicone oils.

The values of m and n in the formula (A) are, respectively, an integer of from 2 to 6. If the polymer of the formula (A) is used in combination with the organohydrogenpolysiloxane of the formula (2), m is preferably an integer of from 3 to 6.

It will be noted that the starting polymers of the formulas (2), (A) and (B) are all known ones and are readily available on the commercial base.

These organohydrogenpolysiloxanes, polyoxyalkylene and/or organopolysiloxane are subjected to addition polymerization provided that the organohydrogenpolysiloxane of the general formula (1) and/or the polyoxyalkylene of the formula (A) should be contained in the polymerization system. The addition polymerization proceeds in the presence of a catalyst such as a platinum or rhodium compound at room temperature or at a temperature of from about 50° C. to 150° C. for a time of from 0.5 to 5 hours. Examples of the platinum compound include chloroplatinic acid, alcohol-modified chloroplatinic acid, chloroplatinic acid-vinyl siloxane complex and the like.

For the addition polymerization, organic solvents may be used, if necessary. Examples of such organic solvents include aliphatic alcohols such as methanol, ethanol, 2-propanol, butanol and the like, aromatic hydrocarbons such as benzene, toluene, xylene and the like, aliphatic and alicyclic hydrocarbons such as n-pentane, n-hexane, cyclohexane and the like, halogenated hydrocarbons such as dichloromethane, chloroform, carbon tetrachloride, trichloroethane, trichloroethylene, fluorinated and chlorinated hydrocarbons and the like. When the composition is used in the fields of medicines and cosmetics, ethanol is preferably used.

The polymer obtained by reaction between the starting polymer of the general formula (1) and/or (2) and the starting polymer of the general formula (A) and/or (B) may be obtained by partial addition reaction between the organohydrogenpolysiloxane which is free of any polyoxyalkylene group and a polyoxyalkylene having an aliphatic unsaturated group at one end thereof, followed by further addition polymerization with an organovinylpolysiloxane without isolation of the partial addition polymerization product.

The polymer according to the invention is a kind of crosslinked product.

In the practice of the invention, a pasty composition comprising the polymer thus obtained is obtained by subjecting 100 parts by weight of the polymer and from 10 to 1000 parts by weight, preferably from 20 to 500 parts by weight, of a silicone oil to kneading under shearing conditions. By this, a uniform composition can be obtained. If the amount of the silicone oil is less than 10 parts by weight, a uniform paste is difficult to obtain. On the contrary, when the amount of the oil exceeds 1000 parts by weight, the resulting composition is not thickened satisfactorily and may not become a paste.

The silicone oils useful in the present invention have preferably a viscosity of not higher than 100 centistokes at 25° C. As a matter of course, the silicone oil may be a mixture of a major proportion of a low viscosity oil having a viscosity of not higher than 100 centistokes and a minor proportion of a high viscosity oil having, for example, 1,000,000 centistokes. Specific examples of the silicone oil include linear or branched methylpolysiloxane, methylphenylpolysiloxane, ethylpolysiloxane, ethylmethylpolysiloxane, ethylphenylpolysiloxane, and cyclic dimethylpolysiloxanes such as octamethylcyclotetrasiloxane, decamethylcyclopentasiloxane and the like.

The kneading under shearing conditions is essential for obtaining a uniform pasty composition with a smooth appearance. Mere mixing is not sufficient to obtain the composition. This is because the polymer is not swollen with a silicone oil to a satisfactory extent and both ingredients are not uniformly miscible with each other, resulting in a non-homogeneous composition. Such a composition has polymer pieces, which have not been sufficiently swollen, left therein and is not smooth to the touch or in appearance.

The kneading under shearing conditions is carried out by the use, for example, of a three-roll mill, a two-roll mill, a sand grinder, a colloid mill, the Gaulin homogenizer or the like. Of these, the three-roll mill is preferred.

The polymer of the present invention has good swelling properties in silicone oils and can yield a uniform pasty composition when kneaded along with silicone oils under shearing conditions. The composition is able to stably disperse powders or pigments therein without settlement as would otherwise be settled down in silicone oils owing to the difference in density between the silicone oil and the powder or pigment. In addition, water is also dispersable in the composition without resorting to any surface active agent, so that the composition will be useful as a base for creams and cake-shaped moldings for cosmetics and products other than drugs.

The invention is more particularly described by way of examples, which should not be construed as limiting the invention thereto.

SYNTHETIC EXAMPLE 1

68.0 g of an organohydrogenpolysiloxane of an average compositional formula

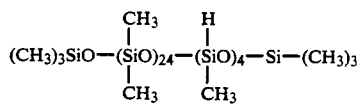

100 g of ethanol, 32 g of a polyoxyalkylene of an average compositional formula, $CH_2=CHCH_2O-(C_2H_4O)_{10}-CH_3$, and 0.3 g of an ethanol solution of 3 wt % of chloroplatinic acid were charged into a reactor, followed by keeping at an inner temperature of from 70° to 80° C. and agitation for 2 hours. Thereafter, the solvent was removed under reduced pressure to obtain an organohydrogenpolysiloxane of the following formula

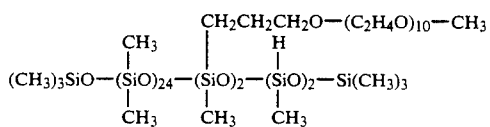

EXAMPLE 1

100.0 g of the organohydrogenpolysiloxane prepared in Synthetic Example 1, 100.0 g of ethanol, 28.9 g of dimethylpolysiloxane terminated with a dimethylvinylsilyl end group at both ends of the following average compositional formula

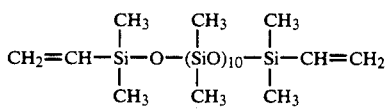

and 0.3 g of an ethanol solution of 3 wt % of chloroplatinic acid were charged into a reactor, and were maintained at an inner temperature of from 70° to 80° C. and agitated for 2 hours. Thereafter, the solvent was removed under reduced pressure to obtain an elastic polymer.

20 parts by weight of the polymer and 80 parts by weight of dimethylpolysiloxane having a viscosity of 6 centistokes were mixed and dispersed, followed by sufficient kneading under shearing conditions by means of a three-roll mill to obtain a silicone composition. The composition was a uniform pasty composition which was soft to the touch and had a viscosity of 32,000 cps.

Thereafter, 50 parts by weight of the silicone composition and 50 parts by weight of water were mixed. As a result, it was found that mere agitation permitted water to be readily dispersed thereby obtaining a uniform creamy composition.

For comparison, a mixture obtained prior to the kneading was agitated at room temperature for 2 hours by means of a planetary mixer instead of the three-roll mill. As a result, the polymer was not uniformly swollen and a pasty composition which was soft and smooth to the touch could not be obtained. Further, water was added to this composition but was not dispersed in the composition. The mixture was separated into two phases of an oil phase and an aqueous phase.

From these results, the polymer of the invention is uniformly swollen in the silicone oil and is able to thicken the oil only when a satisfactory shearing force is applied thereto, thereby yielding a soft pasty composition. On the other hand, unless any shearing force is applied, such a pasty composition as in the above case cannot be obtained.

EXAMPLE 2

100.0 g of the organohydrogenpolysiloxane of the following average compositional formula

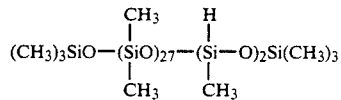

62.0 g of ethanol, 23.6 g of a polyoxyalkylene of the following average compositional formula, $CH_2=CHCH_2O-(C_2H_4O)_{10}-CH_2CH=CH_2$, and 0.3 g of an ethanol solution of 3 wt % of chloroplatinic acid were charged into a reactor, and were maintained at an inner temperature of from 70° to 80° C. and agitated for 2 hours. Thereafter, the solvent was removed under reduced pressure to obtain a particulate polymer.

33 parts by weight of the thus obtained polymer and 67 parts by weight of dimethylpolysiloxane having a viscosity of 6 centistokes were mixed and dispersed, followed by sufficient kneading under shearing conditions by means of a three-roll mill to cause the polymer to be swollen thereby obtaining a silicone composition. The composition was a uniform pasty composition which was soft to the touch and had a viscosity of 24,800 cps. 50 parts by weight of the silicone composition and 50 parts by weight of water were mixed. As a result, it was found that mere agitation permitted water to be readily dispersed thereby obtaining a uniform creamy composition.

EXAMPLE 3

100.0 g of the organohydrogenpolysiloxane of the following average compositional formula as used in Synthetic Example 1

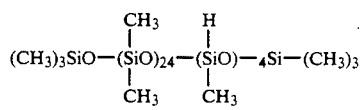

75 g of ethanol, 49.4 g of a polyoxyalkylene of the following average compositional formula used in Example 2, $CH_2=CHCH_2O-(C_2H_4O)_{10}-CH_2CH=CH_2$, and 0.3 g of an ethanol solution of 3 wt % of chloroplatinic acid were charged into a reactor, and were maintained at an inner temperature of from 70° to 80° C. and agitated for 2 hours. Thereafter, the solvent was removed under reduced pressure to obtain a particulate polymer.

33 parts by weight of the thus obtained polymer and 67 parts by weight of dimethylpolysiloxane having a viscosity of 6 centistokes were mixed and dispersed, followed by sufficient kneading under shearing conditions by means of a three-roll mill to cause the polymer to be swollen thereby obtaining a silicone composition. The composition was a uniform paste which was soft to the touch and had a viscosity of 10,600 cps. 50 parts by weight of the silicone composition and 50 parts by weight of water were mixed. As a result, it was found that mere agitation permitted water to be readily dispersed thereby obtaining a uniform creamy composition.

EXAMPLE 4

100.0 g of an organohydrogenpolysiloxane of the following average compositional formula

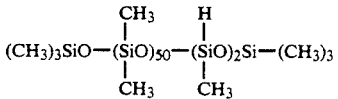

57 g of ethanol, 13.5 g of a polyoxyalkylene of the following average compositional formula used in Example 2, $CH_2=CHCH_2O-(C_2H_4O)_{10}-CH_2CH=CH_2$, and 0.3 g of an ethanol solution of 3 wt % of chloroplatinic acid were charged into a reactor, and were maintained at an inner temperature of from 70° to 80° C. and agitated for 2 hours. Thereafter, the solvent was removed under reduced pressure to obtain a particulate polymer (Composition 1).

20 parts by weight of the thus obtained polymer and 80 parts by weight of dimethylpolysiloxane having a viscosity of 6 centistokes were mixed and dispersed, followed by sufficient kneading under shearing conditions by means of a three-roll mill to cause the polymer to be swollen thereby obtaining a silicone composition (Composition 2). The composition was a uniform paste which was soft to the touch and had a viscosity of 22,800 cps. 50 parts by weight of the silicone composition and 50 parts by weight of water were mixed. As a result, it was found that mere agitation permitted water to be readily dispersed thereby obtaining a uniform creamy composition.

| Application 1: Face cream | |
|---|---|
| Formulation | Parts by Weight |
| 1. Silicone Composition 2 of Example 4 | 10 |
| 2. Trioctanoic acid glyceride | 30 |
| 3. 1,3-Butylene glycol | 20 |
| 4. Purified water | 40 |
| 5. Perfume | |

Preparation:

The ingredients 1 and 2 above were mixed to obtain a oil phase component. The ingredients 3 and 4 were mixed to obtain an aqueous phase component. The thus obtained aqueous phase component was added to the oil phase component under agitation to obtain an emulsion, followed by further addition of the ingredient 5 and packing in a container thereby obtaining a product.

The resultant face cream was well spread and was wet to the touch. In addition, after application, the cream was felt cool with good feeling to the touch and good usability.

| Application 2: Foundation | |
|---|---|
| Formulation | Parts by Weight |
| 1. Composition 1 of Example 4 | 1.6 |
| 2. Dimethylsiloxane (viscosity 6 cps.) | 8.4 |
| 3. Trioctanoic acid glyceride | 4 |
| 4. Diglycerine triisostearate | 6 |
| 5. Squalane | 8 |
| 6. Methylphenylpolysiloxane | 10 |
| 7. Titanium oxide | 23 |
| 8. Mica | 14 |
| 9. Pigment | 5 |
| 10. Purified water | 20 |

Preparation:

The ingredients 1 and 2 were mixed and dispersed, followed by kneading by means of a three-roll mill to cause the polymer to be swollen to obtain a silicone composition. The ingredients 3 to 6 were added to the thus obtained composition to obtain an oil phase composition. Thereafter, the ingredients 7 to 9 were mixed and powdered uniformly, which was added to the oil phase composition, followed by kneading by means of a three-roll mill. While the resulting mixture was agitated, the ingredient 10 was added, followed by packing the mixture in a container to obtain a product.

The thus obtained foundation was free of sticking and was cool to the touch with good spreadability, thereby giving a uniform foundation film and ensuring a makeup to last long.

What is claimed is:

1. A crosslinked silicone polymer which is obtained by addition polymerization in the presence of a catalyst comprising a platinum or rhodium compound of (i) at least one organohydrogenpolysiloxane selected from the group consisting of those of the general formulas (1) and (2), and mixtures thereof, $$R^1{}_aR^2{}_bH_cSiO_{(4-a-b-c)/2} \quad (1)$$

$$R^1{}_jH_kSiO_{(4-j-k)/2} \quad (2)$$

and (ii) at least one member selected from the group consisting of a polyoxyalkylene of the general formula (A)

$$C_mH_{2m-1}O(C_2H_4O)_p(C_3H_6O)_qC_mH_{2m-1} \quad (A)$$

and an organopolysiloxane of the general formula (B)

$$R^1{}_dR^3{}_eSiO_{(4-d-e)/2} \quad (B),$$

and mixtures thereof, provided that at least one of the organohydrogenpolysiloxane of the general formula (1) and the polyoxyalkylene of the general formula (A) is present for the addition polymerization, wherein $R^1$'s may be the same or different in the respective formulas and represent an unsubstituted or substituted alkyl group having from 1 to 18 carbon atoms, an aryl group, or a monovalent halogenated hydrocarbon group, $R^2$ represents an organic group of the general formula, $C_nH_{2n}O(C_2H_4O)_f(C_3H_6O)_gR^4$, wherein $R^4$ represents a hydrogen atom, an alkyl group having from 1 to 5 carbon atoms or a group of the formula, $R^5$—(CO)—, in which $R^5$ represents an alkyl group having from 1 to 5 carbon atoms, each of m and n is an integer of from 2 to 6, f is an integer of from 2 to 200, and g is an integer of from 0 to 200 provided that f+g is in the range of from 3 to 200, $R^3$ represents a monovalent hydrocarbon group having a vinyl end group and having from 2 to 10 carbon atoms, a, b, c, d, e, j and k are, respectively, such that $1.0 \leq a \leq 2.5$, $0.001 \leq b \leq 1$, $0.001 \leq c \leq 1$, $1.0 \leq d \leq 3.0$, $0.001 \leq e \leq 1.5$, $1.0 \leq j \leq 3.0$, and $0.001 \leq k \leq 1.5$, p is an integer of from 2 to 200, and q is an integer of from 0 to 200 provided that p+q is from 3 to 200.

2. A crosslinked silicone polymer according to claim 1, wherein said at least one organohydrogenpolysiloxane (i) is an organohydrogenpolysiloxane of the general formula (1).

3. A crosslinked silicone polymer according to claim 2, wherein said organohydrogenpolysiloxane has a linear structure and comprises $R^1{}_2SiO$ units, $R^1{}_3SiO_{0.5}$ units, $R^2R^1SiO$ units, and $HR^1SiO$ units.

4. A crosslinked silicone polymer according to claim 1, wherein said at least one organohydrogenpolysiloxane (i) is an organohydrogenpolysiloxane of the general formula (2).

5. A crosslinked silicone polymer according to claim 4, wherein said said organohydrogenpolysiloxane has $R^1{}_2SiO$ units, $R^1{}_3SiO_{0.5}$ units, and $R^1HSiO$ units at the same time wherein each $R^1$ has the same meaning as defined in claim 1.

6. A crosslinked silicone polymer according to claim 4, wherein said organohydrogenpolysiloxane of the general formula (2) is subjected to addition polymerization with the polyoxyalkylene of the general formula (A) wherein m is an integer of from 3 to 6.

7. A crosslinked silicone polymer according to claim 1, wherein said at least one organohydrogenpolysiloxane (i) is a mixture of organohydrogenpolysiloxanes of the general formulas (1) and (2).

8. A crosslinked silicone polymer according to claim 1, wherein said at least one member (ii) is the polyoxyalkylene of the general formula (A).

9. A crosslinked silicone polymer according to claim 1, wherein said at least one member (ii) is the organopolysiloxane of the general formula (B).

10. A crosslinked silicone polymer according to claim 9, wherein $R^3$ of the formula (B) contains two carbon atoms.

11. A crosslinked silicone polymer according to claim 1, wherein said at least one member (ii) is a mixture of the polyoxyalkylene of the general formula (A) and the organopolysiloxane of the general formula (B).

12. A crosslinked silicone polymer according to claim 1, wherein $1.9 \leq a \leq 2.1$, $0.01 \leq b \leq 0.50$, $0.01 \leq c \leq 0.10$, $1.9 \leq d \leq 2.1$, $0.01 \leq e \leq 0.50$, $3 \leq f \leq 20$, $0 \leq g \leq 20$, $1.9 \leq j \leq 2.1$, $0.01 \leq k \leq 1.10$, $3 \leq p \leq 20$, and $0 \leq q \leq 20$.

13. A pasty silicone oil composition capable of dispersing water, which comprises a kneaded mixture of:

100 parts by weight of a crosslinked silicone polymer which is obtained by addition polymerization in the presence of a catalyst comprising a platinum or rhodium compound of (i) at least one organohydrogenpolysiloxane selected from the group consisting of those of the general formulas (1) and (2), and mixtures thereof, $$R^1_a R^2_b H_c SiO_{(4-a-b-c)/2} \quad (1)$$

$$R^1_j H_k SiO_{(4-j-k)/2} \quad (2)$$

and (ii) at least one member selected from the group consisting of a polyoxyalkylene of the general formula (A)

$$C_m H_{2m-1} O(C_2H_4O)_p(C_3H_6O)_q C_m H_{2m-1} \quad (A)$$

and an organopolysiloxane of the general formula (B)

$$R^1_d R^3_e SiO_{(4-d-e)/2} \quad (B),$$

and mixtures thereof, provided that at least one of the organohydrogenpolysiloxane of the general formula (1) and the polyoxyalkylene of the general formula (A) is present for the addition polymerization, wherein $R^1$'s may be the same or different in the respective formulas and represent an unsubstituted or substituted alkyl group having from 1 to 18 carbon atoms, an aryl group, or a monovalent halogenated hydrocarbon group, $R^2$ represents an organic group of the general formula, $C_nH_{2n}O(C_2H_4O)_f(C_3H_6O)_gR^4$, wherein $R^4$ represents a hydrogen atom, an alkyl group having from 1 to 5 carbon atoms or a group of the formula, $R^5$—(CO)—, in which $R^5$ represents an alkyl group having from 1 to 5 carbon atoms, each of m and n is an integer of from 2 to 6, f is an integer of from 2 to 200, and g is an integer of from 0 to 200 provided that f+g is in the range of from 3 to 200, $R^3$ represents a monovalent hydrocarbon group having a vinyl end group and having from 2 to 10 carbon atoms, a, b, c, d, e, j and k are, respectively, such that $1.0 \leq a \leq 2.5$, $0.001 \leq b \leq 1$, $0.001 \leq c \leq 1$, $1.0 \leq d \leq 3.0$, $0.001 \leq e \leq 1.5$, $1.0 \leq j \leq 3.0$, and $0.001 \leq k \leq 1.5$, p is an integer of from 2 to 200, and q is an integer of from 0 to 200 provided that p+q is from 3 to 200; and from 10 to 1000 parts by weight of a silicone oil having a viscosity of not higher than 100 centistokes at 25° C., said silicone polymer being swollen with said silicone oil.

14. A pasty silicone oil composition according to claim 13, wherein said silicone oil is at least one member selected from the group consisting of linear or branched methylpolysiloxane, methylphenylpolysiloxane, ethylpolysiloxane, ethylmethylpolysiloxane, ethylphenylpolysiloxane and cyclic dimethylpolysiloxane.

15. A pasty silicone oil composition according to claim 13, wherein said at least one organohydrogenpolysiloxane (i) is an organohydrogenpolysiloxane of the general formula (1).

16. A pasty silicone oil composition according to claim 15, wherein said organohydrogenpolysiloxane has a linear structure and comprises $R^1_2SiO$ units, $R^1_3SiO_{0.5}$ units, $R^2R^1SiO$ units, and $HR^1SiO$ units.

17. A pasty silicone oil composition according to claim 13, wherein said at least one organohydrogenpolysiloxane (i) is an organohydrogenpolysiloxane of the general formula (2).

18. A pasty silicone oil composition according to claim 17, wherein said organohydrogenpolysiloxane of the general formula (2) is subjected to addition polymerization with the polyoxyalkylene of the general formula (A) wherein m is an integer of from 3 to 6.

19. A pasty silicone oil composition according to claim 17, wherein said organohydrogenpolysiloxane has $R^1_2SiO$ units, $R^1_3SiO_{0.5}$ units, and $R^1HSiO$ units at the same time.

20. A pasty silicone oil composition according to claim 13, wherein said at least one organohydrogenpolysiloxane (i) is a mixture of organohydrogenpolysiloxanes of the general formulas (1) and (2).

21. A pasty silicone oil composition according to claim 13, wherein said at least one member (ii) is the polyoxyalkylene of the general formula (A).

22. A pasty silicone oil composition according to claim 13, wherein said at least one member (ii) is the organopolysiloxane of the general formula (B).

23. A pasty silicone oil composition according to claim 22, wherein $R^3$ of the formula (B) contains two carbon atoms.

24. A pasty silicone oil composition according to claim 13, wherein said at least one member is a mixture of the polyoxyalkylene of the general formula (A) and the organopolysiloxane of the general formula (B).

25. A silicone polymer as defined by claim 1, wherein the addition polymerization is conducted at room temperature or at a temperature of from about 50° C. to 150° C., and for a time of from 0.5 to 5 hours.

26. A pasty silicone oil composition as defined by claim 13, wherein the addition polymerization is conducted at room temperature or at a temperature of from about 50° C. to 150° C., and for a time of from 0.5 to 5 hours.

* * * * *